US008845578B2

(12) United States Patent
Sherman et al.

(10) Patent No.: US 8,845,578 B2
(45) Date of Patent: Sep. 30, 2014

(54) BIOMATERIAL DELIVERY DEVICE

(71) Applicant: Medtronic Xomed, Inc., Jacksonville, FL (US)

(72) Inventors: Ethan G. Sherman, Jacksonville, FL (US); Matthew J. Friend, Jacksonville, FL (US); Phillip J. Berman, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 13/781,072

(22) Filed: Feb. 28, 2013

(65) Prior Publication Data

US 2014/0243791 A1   Aug. 28, 2014

(51) Int. Cl.
*A61M 13/00* (2006.01)
*A61M 31/00* (2006.01)

(52) U.S. Cl.
CPC ..................................... *A61M 31/00* (2013.01)
USPC .............. 604/58; 604/500; 604/218; 222/211

(58) Field of Classification Search
CPC ............ A61M 15/00; A61M 15/0065; A61M 2202/064; A61M 11/00; A61M 35/00; A61K 9/00; A61K 9/1652; A61K 9/1605; B01F 11/00; B01F 11/0054; B01F 11/0057; B01F 11/0077; B01F 11/24
USPC .............. 604/500, 218, 58, 59, 311; 222/211, 222/235, 226, 233, 234, 287, 241; 433/90, 433/80, 141, 88, 89; 128/203.15, 203.12, 128/200.23, 200.24
See application file for complete search history.

(56) References Cited

U.S. PATENT DOCUMENTS

| | | |
|---|---|---|
| 39,889 A | 9/1863 | Crossman |
| 1,678,562 A | 7/1928 | Edens |

(Continued)

FOREIGN PATENT DOCUMENTS

| | | |
|---|---|---|
| WO | WO 2008/125402 A1 | 10/2008 |
| WO | WO 2009/132229 A2 | 10/2009 |
| WO | WO 2011/059953 A1 | 5/2011 |
| WO | WO 2011/149436 A1 | 12/2011 |

OTHER PUBLICATIONS

"Eppendorf Combitips® Eppendorf Combitips® Plus" Product Information Sheets, Eppendorf North America, Inc., 8 pages (2005).

(Continued)

*Primary Examiner* — Scott Medway
(74) *Attorney, Agent, or Firm* — IPLM Group, P.A.

(57) ABSTRACT

A biomaterial delivery device includes an elongated handheld powder storage conduit with proximal and distal ends and a bore having a central axis. The proximal end is closed by a movable powder dispensing actuator, and the distal end is closed by an openable sealing nib moveable from its closed to its open position by force upon the actuator whether or not the distal end is in contact with a surface. The conduit contains finely-divided loosely-filled powdered sterile biomaterial and a plurality of powder-contacting clump-disrupting projections arrayed inside and along the length of the conduit between the actuator and the nib. The projections are movable in the direction of the central axis by force upon the actuator, and the device when held upright with the nib opened provides a path along which powder may fall past the projections to be gravitationally dispensed in non-atomized form.

**23 Claims, 4 Drawing

(56) References Cited

U.S. PATENT DOCUMENTS

| | | |
|---|---|---|
| 1,684,999 A | 9/1928 | Levy, Jr. |
| 3,816,921 A | 6/1974 | Malmin |
| 3,948,264 A * | 4/1976 | Wilke et al. .............. 128/203.15 |
| 4,015,753 A | 4/1977 | Bennett |
| 4,261,488 A | 4/1981 | Bennett |
| 4,307,823 A | 12/1981 | Heiss et al. |
| 4,356,941 A | 11/1982 | McRoskey et al. |
| D270,183 S | 8/1983 | Govenius |
| 4,468,218 A | 8/1984 | Armstrong |
| 4,492,576 A | 1/1985 | Dragan |
| 4,801,263 A | 1/1989 | Clark |
| 4,973,246 A | 11/1990 | Black et al. |
| 5,033,463 A | 7/1991 | Cocozza |
| D331,970 S | 12/1992 | Creamer, Jr. |
| 5,244,388 A | 9/1993 | Frush |
| 5,259,537 A | 11/1993 | Beers et al. |
| 5,286,257 A | 2/1994 | Fischer |
| 5,429,122 A * | 7/1995 | Zanen et al. .............. 128/203.15 |
| 5,490,615 A | 2/1996 | Robbins et al. |
| D368,963 S | 4/1996 | Gomes |
| 5,513,630 A | 5/1996 | Century |
| 5,520,174 A | 5/1996 | Evans et al. |
| 5,549,564 A | 8/1996 | Yoon |
| 5,554,136 A | 9/1996 | Luther |
| D374,932 S | 10/1996 | Engelman |
| 5,591,408 A | 1/1997 | Belgardt et al. |
| 5,620,660 A | 4/1997 | Belgardt et al. |
| 5,620,661 A | 4/1997 | Schürbrock |
| 5,624,406 A | 4/1997 | Labouze |
| 5,642,730 A | 7/1997 | Baran |
| D384,162 S | 9/1997 | Husar et al. |
| D384,163 S | 9/1997 | Husar et al. |
| 5,676,130 A | 10/1997 | Gupte et al. |
| D387,426 S | 12/1997 | Husar et al. |
| 5,694,920 A | 12/1997 | Abrams et al. |
| 5,758,967 A | 6/1998 | King |
| 5,800,059 A | 9/1998 | Cooke et al. |
| 5,816,804 A | 10/1998 | Fischer |
| 5,816,805 A | 10/1998 | Cheetham |
| 5,829,434 A | 11/1998 | Ambrosio et al. |
| 6,059,570 A | 5/2000 | Dragan et al. |
| 6,210,377 B1 | 4/2001 | Ouchi |
| 6,238,212 B1 | 5/2001 | Khachatoorian et al. |
| 6,267,269 B1 | 7/2001 | Kates |
| 6,328,033 B1 * | 12/2001 | Avrahami ................ 128/203.15 |
| RE37,760 E | 6/2002 | Mathison et al. |
| 6,408,846 B1 | 6/2002 | Ohki et al. |
| 6,416,322 B2 | 7/2002 | Qualliotine et al. |
| 6,540,072 B1 | 4/2003 | Fischer |
| 6,550,957 B2 * | 4/2003 | Mizutani et al. .............. 366/189 |
| 6,585,511 B2 | 7/2003 | Dragan et al. |
| 6,808,091 B2 | 10/2004 | Njaastad |
| 6,814,072 B1 * | 11/2004 | Seppala .................. 128/203.15 |
| 6,878,338 B2 | 4/2005 | Taylor et al. |
| 6,886,560 B1 | 5/2005 | Seppälä |
| 6,926,003 B2 | 8/2005 | Seppälä |
| 6,976,842 B1 | 12/2005 | Miggantz |
| 6,990,974 B2 * | 1/2006 | Staniforth et al. ........ 128/200.18 |
| 7,040,893 B2 | 5/2006 | Fischer |
| 7,089,934 B2 | 8/2006 | Staniforth et al. |
| 7,179,085 B2 | 2/2007 | Dorsey et al. |
| 7,185,648 B1 | 3/2007 | Rand |
| D554,264 S | 10/2007 | Watson et al. |
| 7,357,789 B2 | 4/2008 | Bills |
| 7,431,587 B2 | 10/2008 | Pond |
| D603,113 S | 10/2009 | Morton |
| 7,740,479 B2 | 6/2010 | Allred |
| 7,834,065 B2 | 11/2010 | Nakajima et al. |
| 7,922,043 B2 | 4/2011 | Luechinger |
| 8,037,880 B2 | 10/2011 | Zhu et al. |
| 8,066,510 B2 | 11/2011 | Ho et al. |
| D655,812 S | 3/2012 | Ramini |
| 8,127,763 B2 | 3/2012 | Smyth et al. |
| 8,132,565 B2 | 3/2012 | Von Schuckmann |
| 8,210,171 B2 * | 7/2012 | Denny et al. ............. 128/203.15 |
| 8,226,599 B2 | 7/2012 | Engle |
| D685,087 S | 6/2013 | Voic |
| D685,466 S | 7/2013 | Moshinsky |
| 8,622,997 B2 | 1/2014 | Shippert |
| 2002/0017295 A1 * | 2/2002 | Weers et al. ............. 128/203.12 |
| 2002/0119417 A1 | 8/2002 | Ashman |
| 2002/0177562 A1 * | 11/2002 | Weickert et al. ................. 514/27 |
| 2005/0005933 A1 | 1/2005 | Seppäläet al. |
| 2006/0100572 A1 | 5/2006 | DiMatteo et al. |
| 2007/0151562 A1 | 7/2007 | Jones et al. |
| 2007/0264310 A1 | 11/2007 | Hissong et al. |
| 2007/0272763 A1 | 11/2007 | Dunne et al. |
| 2008/0168987 A1 * | 7/2008 | Denny et al. ............. 128/203.15 |
| 2008/0185000 A1 | 8/2008 | Schuckmann |
| 2008/0223365 A1 | 9/2008 | Von Schuckmann |
| 2008/0281289 A1 | 11/2008 | Lewis |
| 2009/0013994 A1 | 1/2009 | Jones et al. |
| 2009/0025721 A1 | 1/2009 | Ellwanger et al. |
| 2009/0142728 A1 | 6/2009 | Lawter et al. |
| 2009/0227943 A1 | 9/2009 | Schultz |
| 2009/0260626 A1 | 10/2009 | Von Schuckmann |
| 2009/0291911 A1 | 11/2009 | Myntti et al. |
| 2010/0300441 A1 | 12/2010 | Von Schuckmann et al. |
| 2011/0036870 A1 | 2/2011 | Lüchinger |
| 2011/0178495 A1 | 7/2011 | Ji |
| 2011/0220242 A1 | 9/2011 | Yang et al. |
| 2011/0251580 A1 | 10/2011 | Greenhalgh et al. |
| 2012/0103332 A1 | 5/2012 | Parsons |
| 2012/0108509 A1 | 5/2012 | Hissong et al. |
| 2012/0111326 A1 | 5/2012 | Mayer et al. |
| 2013/0000639 A1 | 1/2013 | Galluppi et al. |

OTHER PUBLICATIONS

Arista® Absorbable Hemostatic Particles AH Product Information Sheets, Medafor Hemostatic Polymer Technologies, 3 pages downloaded from http://www.medafor.com/products/arista.aspx on May 2, 2012.

DryPette® Hand Held Manual Powder Dispensing System, Product Information Sheets, Zinsser Analytic, 4 pages (2009).

* cited by examiner

BIOMATERIAL DELIVERY DEVICE

FIELD OF THE INVENTION

This invention relates to devices for delivering hygroscopic powdered biomaterials to surgical sites located in or near the respiratory tract.

BACKGROUND

Adenoids (pharyngeal tonsils) and tonsils (palatine tonsils) are involved in a number of diseases of the ear, nose, and throat including chronic otitis media with effusion (COME), recurrent acute otitis media (RAOM), adenoiditis, pediatric chronic sinusitis, tonsillitis, pediatric obstructive sleep apnea (OSA), adult OSA, and chronic strep throat. Lingual tonsils can become infected and may cause or aggravate sore throat pain. Initial treatment for these various conditions normally involves administration of oral medications or, in the case of pediatric and adult sleep apnea, use of a continuous positive airway pressure (CPAP) device. Otitis media may be treated using ventilation tube surgery. Treatment success rates are often less than optimal, and in many cases the tonsils, adenoids or other throat tissue eventually may be surgically removed. Such surgeries are however painful, typically require the administration of anesthetics and lengthy post-operative recovery periods, and may be accompanied by complications such as post-operative bleeding, dehydration, weight loss, peritonsillar abscess, torticilis (neck stiffness), tissue regrowth, repeat surgery to address incomplete prior tissue removal, continued COME or RAOM, continued OSA, and occasionally death. Existing post-surgical treatments generally provide only limited relief, and may include dietary limitations, rinses, and administration of painkilling medications or oral antibiotics to reduce post-operative pain and infections.

U.S. Patent Application Publication No. US 2012/0108509 A1 (the disclosure of which is incorporated herein by reference) describes an artificial scab composition for use in tonsillectomy, adenoidectomy and uvulopalatopharyngoplasty (UPPP) procedures. The composition is a substantially dry, free-flowing powdered mixture of at least partially solvatable chitosan particles and at least partially solvatable oxidized polysaccharide particles. When applied to a surgical site or wound moistened with bodily fluids, the powdered mixture forms an inhomogeneous, uncohesive, solid sheet-like body that breaks apart into smaller pieces if peeled away from the surgical site or wound. The powdered mixture may for example be applied using a bellows-type dispenser that expels the powder through an elongated, flexible straw that directs a stream of the powder onto a surgical site.

SUMMARY OF THE INVENTION

If not aimed carefully or if excessive force is applied to the bellows, the above-described dispenser can inadvertently direct some or all of the powdered mixture into a human patient airway rather than on to the intended surgical site. Doing so is undesirable for a variety of reasons including potential patient safety risk and added delay in completing a surgical procedure.

In general, hygroscopic powders are desirable in order to obtain good adhesion to the intended surgical site and rapid formation of the described artificial scab. However, hygroscopic powders also are very prone to clump formation, especially if the powder encounters an obstruction while being dispensed, or if the powder is subjected to pressure while being dispensed. This can interfere with or prevent controllable and accurate powder dispensing.

From the foregoing, it will be appreciated that what is needed in the art is a powdered biomaterial delivery device that can dispense hygroscopic powders in tonsillectomy, adenoidectomy, UPPP and other surgical procedures near patient airways. Such devices and methods for their use are disclosed and claimed herein.

The invention provides in one aspect a biomaterial delivery device comprising an elongated handheld powder storage conduit sized for use in the mouth of a human patient, the conduit having a proximal end, a distal end, and a bore having a central axis, the proximal end being closed by a movable powder dispensing actuator, the distal end being closed by an openable sealing nib that can be moved from its closed to its open position by force upon the actuator whether or not the distal end is in contact with a surface, the conduit containing finely-divided loosely-filled powdered sterile biomaterial and a plurality of powder-contacting clump-disrupting projections, the projections being arrayed inside and along the length of the conduit between the actuator and the nib and being movable in the direction of the central axis by force upon the actuator, wherein the device when held with its proximal end uppermost and the nib actuated to its open position provides a path along which powder may fall past the projections to be gravitationally dispensed in non-atomized form.

The invention provides in another aspect a method for applying a powdered biomaterial to a surgical site near a supine human patient airway, the method comprising the steps of:

a) holding in a generally upright position an elongated handheld powder storage conduit, the conduit having a proximal end, a distal end, and a bore having a central axis, the proximal end being closed by a movable powder dispensing actuator, the distal end being closed by an openable sealing nib that can be moved from its closed to its open position by force upon the actuator whether or not the distal end is in contact with the patient, the conduit containing finely-divided loosely-filled powdered sterile biomaterial and a plurality of powder-contacting clump-disrupting projections, the projections being arrayed inside and along the length of the conduit between the actuator and the nib and being movable in the direction of the central axis by force upon the actuator, and b) repeatedly applying force to the actuator so that powder is dispensed in non-atomized form and in a series of incremental portions past the nib and towards the surgical site.

The disclosed device and method enable rapid and accurate administration of clump-prone sterile powdered biomaterials onto or into surgical site near an airway of a supine patient. The disclosed nib desirably serves as a dump valve, and the disclosed projections desirably break up the falling powder and discourage clump formation. The disclosed device and method desirably permit powder dispensing using gravitational assistance, and without requiring the application of pressure on a cross-section of the powder itself (e.g., from a piston, plunger, compressed gas or other propellant) to force out each incremental powder portion. This helps avoid powder clumping and clogging inside the delivery device and powder atomization at the delivery site, facilitates rapid and readily controllable operation by surgical personnel, and helps minimize inadvertent misdirection of biomaterial powder into the patient airway rather than into or onto the intended surgical site.

BRIEF DESCRIPTION OF THE DRAWING

Like reference symbols in the various figures of the drawing indicate like elements.

DETAILED DESCRIPTION

The following detailed description describes certain embodiments and is not to be taken in a limiting sense. The terms shown below have the following meanings:

The term "airway" means a mammalian breathing passage, e.g., as formed by the mouth, nose, throat and trachea.

The term "average inside diameter" when used in reference to a filled powdered delivery device having (a) a distal powder delivery outlet and (b) a powder-containing conduit having a central axis, a cylindrical or other cross-section and a constant or varying cross-sectional area along that axis means the diameter of a right circular cylinder having a height and volume like the height and volume circumscribed by the powder when the central axis of the filled device is aligned vertically with the outlet closed and directed downward.

The term "biomaterial" when used in reference to a substance means that the substance may be introduced into (and if need be left in) the body of a patient as part of a surgical procedure without significant deleterious or untoward effects upon the body.

The term "free-flowing" when used in reference to a powdered material means the powder will spontaneously flow downhill when placed on a horizontal surface and the surface rotated to an inclination of about 45° to 60° from the horizontal.

The term "gravitational assistance" when used in reference to a powdered substance dispensed from an outlet means that the substance passes through the outlet primarily due to the influence of gravitational forces.

The term "hygroscopic" when used in reference to a powdered substance means that the substance takes up and retains water while in solid form (for example, by adsorption, absorption, or as chemically-bound water of hydration).

The term "loosely-filled" when used in reference to a powdered substance in a conduit or other container means that the substance is not packed into the container and will rearrange itself within the container if the container is slowly inverted without shaking.

The term "non-atomized" when used in reference to a powdered substance dispensed from an outlet means that a gaseous propellant is not used to accelerate the substance through the outlet or past the outlet (e.g., via the Bernoulli effect).

Figure 1:
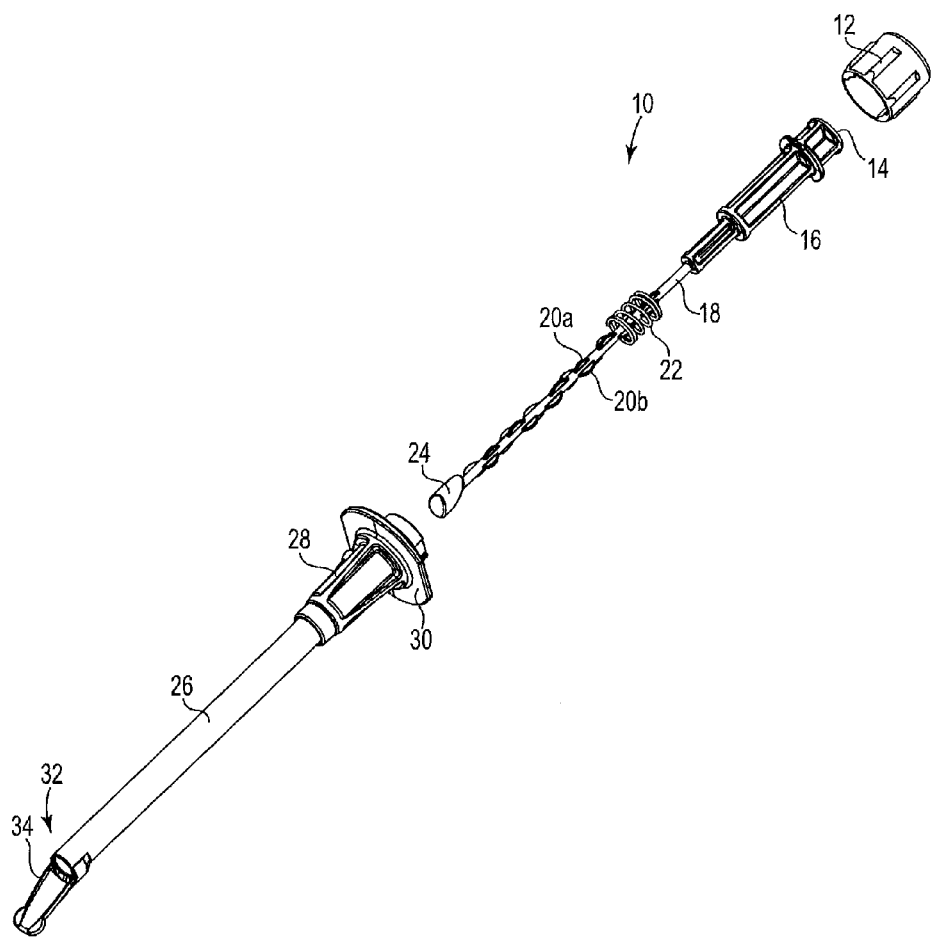
FIG. 1 is an exploded view of one embodiment of the disclosed biomaterial dispensing device.

FIG. 1 is a perspective exploded view depicting components that may be used in an embodiment 10 of the disclosed biomaterial delivery device. Retainer 12 is located at the proximal end of device 10 and provides a sleeve with openings sized to fit over and capture the end 14 of powder dispensing actuator 16. In the embodiment shown in FIG. 1, actuator 16 is integrally molded with an elongated and generally cylindrical, rod-like or stem-like member 18. A plurality of rounded powder-contacting clump-disrupting blade-like projections such as projections 20a and 20b are arrayed along the length of and project outwardly from member 18. Spring 22 biases actuator 16 toward the proximal end of device 10. Nib 24 at the distal end of elongated member 18 serves as a dump valve for a finely-divided loosely-filled powdered sterile biomaterial powder (not shown in FIG. 1) that will be contained in and dispensed by device 10. In the embodiment shown in FIG. 1, nib 24 may be operated by depressing actuator 16 toward the distal end of device 10. The projections on member 18 desirably are sized to fit loosely inside the bore of generally cylindrical or barrel-shaped conduit 26 so that powder may flow and preferably freely flow between projections 20a and 20b and the inner sidewalls of conduit 26. In the embodiment shown in FIG. 1, conduit 26 has a central cylindrical bore having a uniform inside diameter (and accordingly the same value for its average inside diameter) and a central axis, common with the central axis of elongated member 18, along which the movable components of device 10 may reciprocally move towards and away from the distal end of device 10. In the embodiment shown in FIG. 1, the device central axis and the conduit or bore central axis are the same, and unless the context clearly indicates otherwise these terms may be used interchangeably. Actuator 16 desirably is sized to fit snugly but slidably inside a complementary cylindrical opening in grip 28. Flange 30 on grip 28 assists a user of device 10 in holding, moving and actuating device 10 in one gloved hand, for example by holding device 10 with grip 28 placed between, and the distal surface of flange 30 in contact with, the user's gloved thumb and second finger or gloved first and second fingers, while meanwhile depressing actuator 16 using the free gloved index finger or free gloved thumb of the same hand. Meanwhile the user desirably may also tilt, rotate, press against, withdraw from or otherwise move device 10 as need be with respect to the surgical site.

Device 10 may optionally include a projecting powder discharge chute or tip that guides the dispensed powder towards a surgical site while spacing the distal outlet end and nib of device 10 away from the site. Doing so provides a tissue-contacting working end surface in the device that helps minimize moisture entry into device outlet 32 and discourages clogging at the consequently remotely-located device outlet. The tip may be removable by a user and replaceable or interchangeable with other tips having different sizes (e.g., pediatric and adult sizes) or different shapes or anatomically specific features that better adapt the tip to the intended surgical site, for example by providing specialized working surfaces that assist in depositing or spreading the biomaterial in complex or unusual surgical sites. One exemplary chute design is shown as tip 34 in FIG. 1, and further details regarding its configuration, the corresponding nib configuration and their relationship or regarding the presently-disclosed device may be found in copending U.S. patent application Ser. No. 13/781,331, 29/447,060 and 29/447,079 filed even date herewith and the disclosures of which are incorporated herein by reference.

Figure 2:
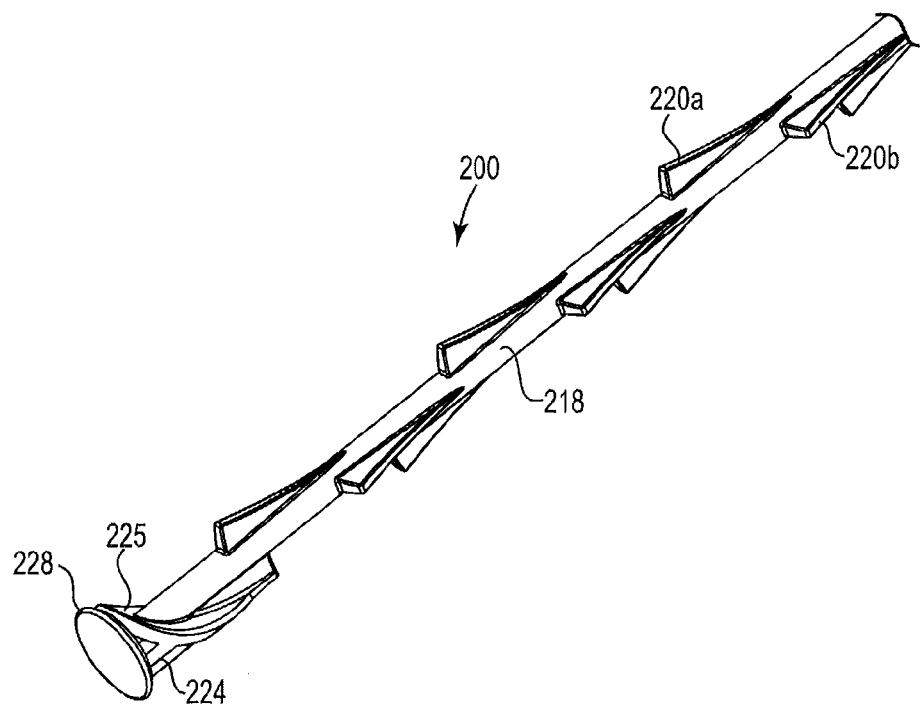
FIG. 2 is a perspective view of a component for use in the disclosed device.

FIG. 2 depicts a perspective view of a portion of another embodiment of the disclosed biomaterial delivery device. Component 200 includes an elongated and generally cylindrical, rod-like or stem-like member 218 along which are arrayed a plurality of triangular or wedge-like powder-contacting clump-disrupting blade-like projections such as projections 220a and 220b. Nib 224 includes a ramp 225 that directs substantially all the dispensed powder portion away from the central axis of member 218. Discharge outlet sealing surface 228 discourages powder from passing out of (and discourages powder, liquids and other materials from entering) the conduit when nib 224 is in its closed position.

Figure 3:
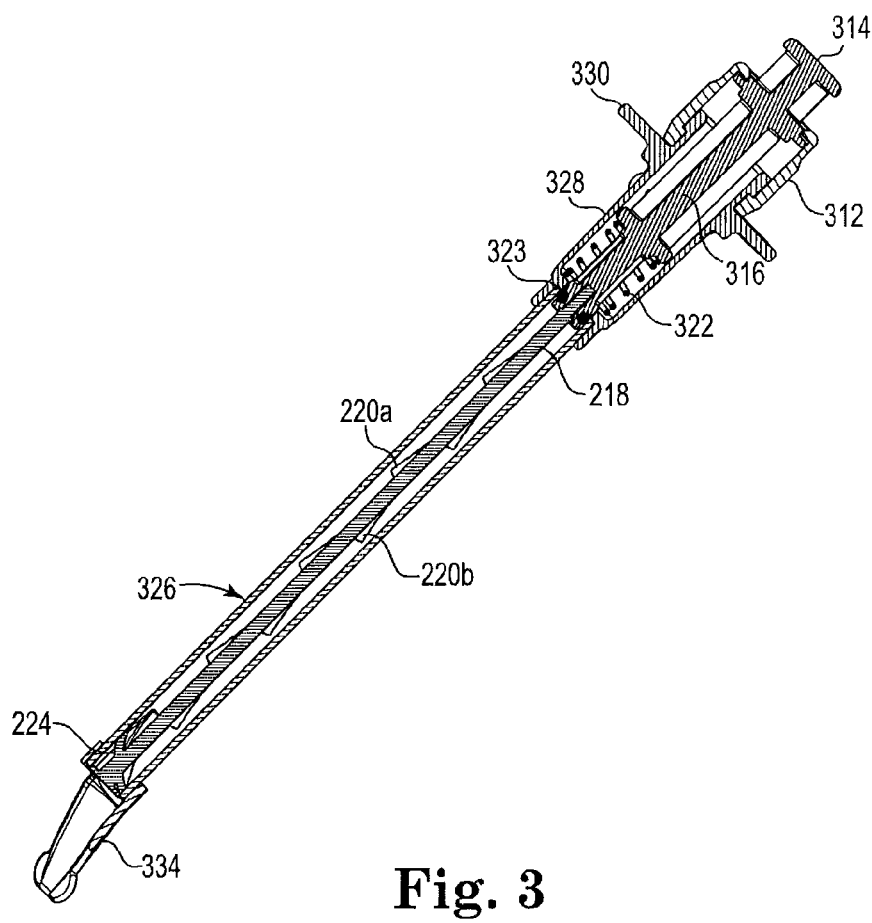
FIG. 3 is a cross-sectional view of one embodiment of the disclosed device using the FIG. 2 component.
Figure 4:
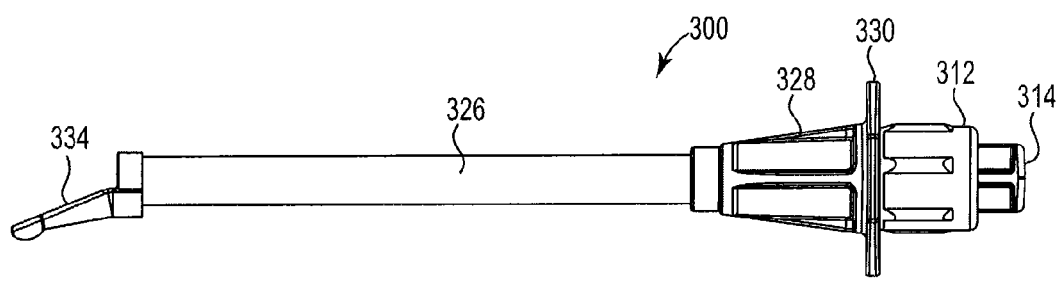
FIG. 4 is a side orthogonal view of the assembled FIG. 3 device.

FIG. 3 depicts a cross-sectional view of an embodiment 300 of the disclosed device. Device 300 resembles the device shown in FIG. 1 but employs elongated member 218 with its wedge-like powder-contacting clump-disrupting blade-like projections 220*a* and 220*b* and nib 224 as shown in FIG. 2. Device 300 also includes retainer 312, proximally-projecting end 314 of powder dispensing actuator 316, spring 322, sealing O-ring 323, conduit 326, grip 328, flange 330 and tip 334. As depicted in FIG. 3, the projections are sized so they do not touch the bore sidewall. FIG. 4 depicts a side orthogonal view of the assembled FIG. 3 device.

Figure 5:
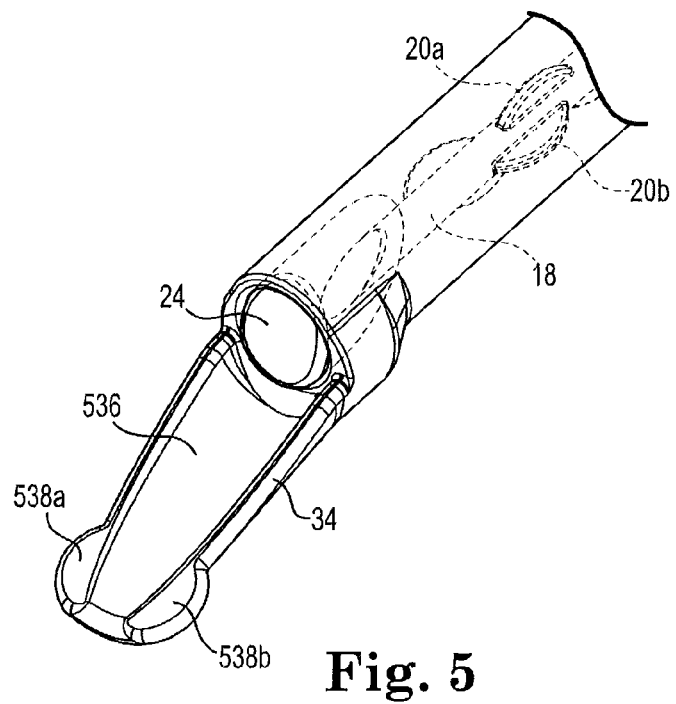
FIG. 5 is a perspective distal end view of the assembled FIG. 1 device showing the nib in its closed position.
Figure 6:
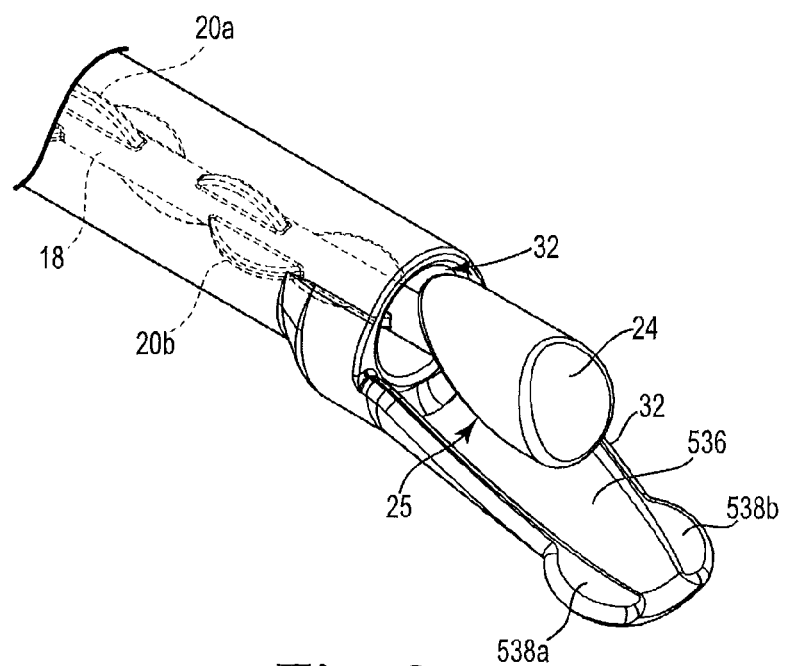
FIG. 6 is a perspective distal end view of the assembled FIG. 1 device showing the nib in its open position.

FIG. 5 and FIG. 6 respectively depict perspective distal end portion views of the assembled FIG. 1 device showing nib 24 in its closed (FIG. 5) and open (FIG. 6) positions. In the embodiment shown in FIG. 5 and FIG. 6, opening and closing nib 24 also causes elongated member 18 and projections such as projections 20*a* and 20*b* to move through at least some of the powder, thereby discouraging clumping, helping to break up already-formed clumps, and encouraging the powder particles to move (e.g., fall) toward and through the device outlet. In the open nib 24 position, ramp 25 directs falling powder exiting through device outlet 32 away from the central axis of the disclosed device and into chute 536 in tip 34. Gently-rounded wing portions 538*a* and 538*b* and the gently-rounded backside of tip 34 may be used to manipulate (for example, retract) tissue and to rake and spread the dispensed powder across the floor and up and down the sidewalls of the tonsillar fascia. The angled orientation of tip 34 (viz., at an acute angle with respect to the central axis of the assembled device) further assists a user in retracting tissue, raking dispensed powder backwards across the tonsillar fascia floor, raking dispensed powder up the sidewalls of and into pockets or pillars in the tonsillar fascia, and lining up the device outlet above the region at which dispensed powder is desired to land. The tip 34 angle and the complementary ramp 25 angle may each or both be chosen to help regulate the dispensed powder flow rate. The gently-rounded contours and the absence of sharp edges on nib 24 and tip 34 help minimize surgical site trauma while device 10 is being used to dispense, distribute or spread powder.

The disclosed biomaterial delivery device may be made in a variety of other embodiments. A number of design goals may be borne in mind when doing so. For example, the device is as mentioned sized for use in the mouth of a human patient, and desirably is sized for use above surgical sites located in the back of the throat of a supine human patient of adolescent or adult age. In general for such use there will be a desirable balance between the thinness of the device and the rapidity with which it can be used to dispense a needed quantity of biomaterial powder. Desirably the device when inserted through an open patient mouth and directed towards the tonsillar fascia is sufficiently thin so as to leave ample viewing room and space to insert and if need be to operate or manipulate other instruments or objects such as suction lines, lights, retractors (e.g., Hurd retractors) or fingers, e.g., for a hand other than the hand used to operate the disclosed device. The device desirably also is sufficiently long so that the dispenser when so inserted and directed will reach the back of the patient's throat. The device desirably has sufficiently great powder capacity and sufficiently rapid powder delivery capability to enable the desired powder amount to be dispensed, distributed and spread as need be in minimal time, e.g., in less than two minutes, less than one minute or less than 30 seconds per tonsillar fascia for a tonsillectomy procedure. The device desirably provides a line of site view enabling a user to see simultaneously the distal end of the device, previously dispensed powder and the area on which powder will be dispensed with the next device actuation. The device desirably is shaped to enable handheld, one-hand operation using either hand. The device may however be made in a variety of diameters and lengths, and may for example have a conduit with an outer diameter of about 4 to about 15 mm, an average inside diameter of about 5 to about 13 mm, and a length measured from the finger grip to the device outlet of about 10 to about 20 cm for use on tonsillar fascia and longer lengths (for example about 10 to about 25 cm) for use in nasal and sinus procedures. The disclosed flange desirably has a diameter of about 20 to about 40 mm, and may be equipped with flattened circumferential portions to keep the device from rolling when placed on a tray, table or other horizontal surface.

Desirably the device can be rotated at least 360° around its central axis while in the mouth. e.g., in order to switch from right-handed to left-handed use, or to facilitate reorientation of the device such as when changing from one tonsillar fascia to the other. Accordingly, the device desirably does not include airlines or other potentially interfering appendages.

The device desirably includes the disclosed optional tip. When so equipped the device desirably can be used by itself to both dispense and spread metered amounts of powder and form a continuous powder coating over the entire surgical site. Whether or not so equipped, the device desirably is straight along the entire length of the conduit, as that can provide better visibility during use, and can provide better leverage and control if the optional tip is used to distribute or spread the powder.

The device desirably meters out an incremental powder portion each time the actuator is operated. The metered amount will be a function of several factors including the actuator stroke length and geometry, the chosen design for the elongated member (if used) and projections, the chosen design for any seals employed, the device outlet size and shape, and the chosen nib design, tip design and associated angles. The device desirably permits dispensing to occur whether or not the device distal end is in contact with tissue or other surface, and desirably may be operated from its proximal end to dispense powder while the distal end is inserted in a patient's mouth without touching the back of the throat. The device also desirably permits dispensing to occur without having to shake the device. The device desirably is non-pressurized ("non-air-assisted"), does not aerosolize the dispensed powder, and delivers most or all of the dispensed powder to the intended surgical site and none or substantially none of the dispensed powder to the surrounding tissue or the patient airway. The device accordingly would not be regarded as an inhaler. The delivered biomaterial desirably falls down the conduit and through the device outlet primarily or exclusively due to gravitational forces, and desirably is not forced out of the device due to the action of a piston or other component that applies force to the entire cross-sectional area of the dispensed powder portion. The device preferably does not dispense powder or at least a significant quantity of powder if the device outlet is opened while the device is horizontal. The device desirably keeps its powder dry until such time as the dispensed biomaterial contacts the surgical site. Desirably at least the portion of the device housing the stored biomaterial (e.g., the conduit) and optionally also the elongated member (if used), projections or optional tip are transparent or translucent. The use of transparent or translucent components can assist a surgeon in metering a desired powder amount during a procedure and at least initially in seeing where best to spread the powder.

The disclosed actuator preferably has a reciprocating actuation motion and more preferably a reciprocating motion along the device central axis. The motion desirably is in the distal direction, although an upward actuation in the proximal direction could be employed by using a suitable ledge or grip to facilitate lifting the actuator. The actuator may if desired use a rotating actuation motion but desirably does not do so as such actuation may be more difficult to carry out while holding the device in a single gloved hand. For actuation using a reciprocating motion along the device central axis, actuation desirably requires a relatively short (e.g., about 2 to about 12, about 4 to about 12 or about 6 to about 10 mm) stroke and a moderate but noticeable (e.g., about 1 to about 4 Kg) force. Desirably the actuator (or if desired, one or more other components such as a projection or projections or the nib) is provided with one or more small ribbed or grooved portions that engage a nearby complementary recess or tang so as to provide a click stop or other tactile feedback actuation feature. The recited tactile feedback may for example occur during or at the end of an actuation stroke. The tactile feedback may also provide accompanying vibrations that can help agitate the powder. The disclosed actuator, elongated member (if used), projections and nib desirably are connected to one another so that actuation causes all to move (e.g., reciprocate) together. The actuator also desirably is provided as part of an integrally molded component that also includes at least the projections and nib.

The projections function as a "deagglomerator" or "agitator" that helps breaks up the powder as it falls down the conduit, thereby discouraging clump formation and obstruction of the conduit bore and device outlet. The projections may as discussed above be arranged along an elongated (and supporting) member. The elongated member may be centrally located in the conduit bore or may be displaced with respect to the bore central axis. For reasons including good deagglomeration performance and molding convenience, the projections preferably project outwardly from a centrally-located elongated member or support rod, and provide a plurality of axially-spaced and rotationally-staggered projections arrayed along the length of the elongated member. However, if desired the projections could be arrayed along (and for example be integral with) the bore sidewall so that they project inward rather than outward. The projections desirably are arrayed along more than half the powder-containing length of the filled device. The projections may extend further into the powder near the device distal end than at locations nearer the device proximal end. Preferably the projections do not serve as a conventional auger (viz., a rotating conveying device that advances a solid material along the length of a conduit) or static mixer (viz., a multistage fixed mixing device that divides streams of a flowing gas or liquid into twice as many streams at each mixer stage). The projections may undergo both movement in the direction of the central axis and a small rotational movement (e.g., 2, 4, 6 or more degrees) around that axis with each device actuation. However, for some powders it will be better if the projections move only in the direction of the central axis and do not rotate around the central axis during device actuation. Also, for some powders it will be best if the projections, even when motionless, do not impart rotational forces to the falling powder. The projections do however move and most preferably reciprocate axially during actuation of the device. Also, when so moving the projections preferably move with respect to some but not all of the nearby powder. The projections may be uniformly or non-uniformly spaced and oriented along the length of the conduit, with nonuniform spacing or nonuniform orientation being preferred. The projections may have a variety of shapes, including rounded, rectangular, trapezoidal, barbed or other shapes. The projections preferably are sufficiently small so as not to fill the conduit bore, and may for example have a minimum clearance of about 1 to about 3 mm between the widest part of the largest projection and any nearby components such as the bore sidewall. This can help discourage powder clumping and conduit blockage. If the projections are arrayed along the disclosed elongated member, the member preferably has a small diameter (for example, about 2 to about 5 mm) in order to facilitate unhindered passage of the falling powder.

The disclosed nib desirably serves as both a closure valve for the device outlet and as a deflector that directs falling powder away from the device central axis and preferably onto a complementary chute structure in the optional tip. The nib may for example be connected to the actuator via the disclosed elongated member or may be opened and closed using some other connecting structure. Preferably the nib, elongated member and projections are formed (e.g., molded) as a single integral component. The last (viz., most distal) projection may be contiguous with or spaced proximally from the nib. A contiguous arrangement may help prevent powder from forming clumps in the chock or valve sealing region between the nib and the device outlet. The nib preferably discourages the powdered biomaterial from falling into areas where it is not intended to be placed and preferably also provides tactile feedback of dispenser actuation.

The disclosed conduit preferably has a bore (and most preferably a circular bore) whose diameter does not diminish along the length of the device from its proximal to distal ends. Reductions in bore diameter near the proximal end may not be a matter of concern, but reductions in bore diameter near the distal end and especially near the device outlet desirably are avoided. The device outlet preferably has the same cross-sectional shape as the bore (e.g., is circular for a circular bore), preferably is as large as possible, and preferably has a diameter at least 75%, at least 80%, at least 90% or at least as large as the conduit average inside diameter.

The disclosed device and its non-powdered components may be made from a variety of materials including acrylics, olefins such as polyethylene and polypropylene, polycarbonates and other suitable thermoplastic or thermoset materials. The chosen materials desirably have a low tendency to adhere to the chosen biomaterial powder whether due to static or other attractive forces. The device may also include antistatic surface treatments, antistatic additives or surface finishes chosen so as to further discourage powder adhesion.

A wide variety of powdered biomaterials may be packaged in the disclosed device. The biomaterials preferably are organic but for some surgical end uses may be inorganic materials (e.g., calcium carbonates, zeolites and other minerals or salts). Exemplary biomaterials may for example be natural materials (e.g., polysaccharides), chemically modified natural materials (e.g, polysaccharide reaction products including oxidized, acetylated, deacetylated, acid-reacted, anhydride-reacted, esterified, neutralized, base-reacted, vinyl-group reacted, isocyanate-reacted or otherwise functionalized polysaccharides, polysaccharide salts and other polysaccharide derivatives), or synthetic materials (e.g., polyglycolides, polyactides, poly(lactide-co-glycolides), poly(ϵ-caprolactones), poly(dioxanones), polyanhydrides, polyorthoesters, polyethylene glycols and polyvinyl alcohols). The powder may be a single material or mixture of materials (for example, a mixture of a crosslinkable material and a crosslinker). Exemplary biomaterials include agars, alginates, carrageenans, celluloses, chitins, chitosan, chondroitin sulfates, dextrans, galactomannans, glycogens, hyaluronic acids, starches, oxidized cellulose, oxidized chitin, oxidized chitosan, oxidized chondroitin sulfate, oxidized dextran, oxidized glycogen, oxidized hyaluronic acid, oxidized starch and other materials that will be known to persons having ordinary skill in the art. Suitable biomaterials may be obtained from a variety of commercial sources including CarboMer Inc., Monomer-Polymer and Dajac Labs, Inc. and Sigma-Aldrich Co. The powdered biomaterial desirably is obtained in dry particulate form, for example, as free-flowing granules whose average particle diameter is less than about 1 mm, less than about 100 µm, about 1 to about 80 µm, or less than 1 µm. The powdered biomaterial may be comminuted, lyophilized, crystallized or recrystallized if desired. If a mixture of particles is employed, the particles desirably are intimately mixed together prior to placement in the device, and further mixing desirably is not required at the point of use. The biomaterial may provide a variety of features such as the formation of a protective, mucoadhesive, biodegradable, bioresorbable, drug eluting or hemostatic structure (e.g., a layer) following application to a surgical site. The biomaterial preferably is substantially collagen-free and more preferably contains no collagen at all so as to be saleable worldwide for use without restriction in humans. The biomaterial may optionally include a variety of other ingredients that are themselves dry, or which when mixed with the biomaterial will provide or can be processed (e.g., dried) to provide a dry powdered biomaterial. Exemplary such other ingredients include acids, antifoam agents, antimicrobial agents, antioxidants, antistatic agents, bases, buffering agents, colorants, flow aids, hyperosmolar agents, indicators, flavoring agents, sweetening agents, therapeutic agents, modifiers to alter the release rate of therapeutic agents, and other adjuvants that will be familiar to persons having ordinary skill in the art. For example, a useful list of therapeutic agents may be found in U.S. Patent Application Publication No. US 2007/0264310 A1. The biomaterials desirably do not contain ingredients which might potentially harm mucosal tissues or structures. The disclosed device is especially desirable for dispensing hygroscopic powders that are prone to clumping or sticking. The disclosed device desirably contains the total volume of material to be used in an intended surgical procedure, for example about 0.5 to 2 grams per device for tonsillectomy procedures.

The disclosed devices desirably are ready-to use items designed for one-time use. Following filling with the desired biomaterial powder, the device typically will be placed in suitable sealed packaging (for example, a metalized foil pouch and optional box) and subjected to sterilization prior to shipment to an end user. Exemplary sterilization techniques will be familiar to persons having ordinary skill in the art, and include gamma radiation, electron beam (E-Beam) processing, and cold ionizing radiation sterilization (e.g., cold E-Beam sterilization) as described in published PCT Application No. WO 2009/132229 A2.

The disclosed device typically will be used by a surgeon near the conclusion of a surgical procedure. For example, a tonsillectomy or adenoidectomy may be carried out using traditional steps, with tissue excavation being performed using electrocauterization, snares, scalpels or other techniques, followed promptly thereafter by use of the device to dispense and desirably also to distribute or spread a coating of the disclosed powdered biomaterial on the exposed fascia. The application technique is not unlike frosting a cake using the backside of a spoon, but may be carried out much more quickly. Some surgeons may prefer to apply several metered powder doses and then spread the powder, and others may prefer repeatedly to apply a powder dose, spread the powder and repeat until a desired degree of coating is obtained. As a general guide, a desirable application rate may be about 10-25 actuations per tonsil dispensing about 0.02 to 0.05 g per actuation stroke.

Although specific and in some cases preferred embodiments have been illustrated and described, it will be appreciated by those of ordinary skill in the art that a wide variety of alternate or equivalent embodiments calculated to achieve the same purposes may be substituted for the specific embodiments shown and described without departing from the present invention. This application is intended to cover any adaptations or variations of the preferred embodiments discussed herein. Therefore, it is manifestly intended that this invention be limited only by the claims and the equivalents thereof.

We claim:

1. A biomaterial delivery device comprising an elongated handheld powder storage conduit sized for use in the mouth of a human patient, the conduit having a proximal end, a distal end, and a bore having a central axis, the proximal end being closed by a movable powder dispensing actuator, the distal end being closed by an openable sealing nib that can be moved from its closed to its open position by force upon the actuator whether or not the distal end is in contact with a surface, the conduit containing finely-divided loosely-filled powdered sterile biomaterial and a plurality of powder-contacting clump-disrupting projections, the projections being arrayed inside and along the length of the conduit between the actuator and the nib and being movable in the direction of the central axis by force upon the actuator, wherein the device when held with its proximal end uppermost and the nib actuated to its open position provides a path along which powder falls past the projections and past the nib and is gravitationally dispensed from the device in non-aerosolized form.

2. A device according to claim 1 wherein the powder is free-flowing and hygroscopic.

3. A device according to claim 1 wherein the powder comprises a polysaccharide, polysaccharide reaction product or polysaccharide derivative.

4. A device according to claim 1 wherein the actuator dispenses about 0.02 to 0.05 g powder per actuation.

5. A device according to claim 1 wherein the actuator has one or more ribbed or grooved portions that engage a complementary recess or tang so as to provide a click stop or other tactile feedback actuation feature during movement of the actuator.

6. A device according to claim 1 wherein the nib comprises a discharge outlet sealing surface that discourages liquids from entering the conduit when the nib is in its closed position.

7. A device according to claim 1 wherein the projections are arranged along and project outwardly from an elongated member centrally located in the bore.

8. A device according to claim 7 wherein the projections are axially-spaced, rotationally-staggered and arrayed along the length of the elongated member.

9. A device according to claim 1 wherein the device has a powder-containing portion having a length along the central axis, and the projections are arrayed along more than half the powder-containing portion length.

10. A device according to claim 1 wherein the device has a powder-containing portion having a length along the central axis, and the projections are non-uniformly spaced or non-uniformly oriented along the powder-containing portion length.

11. A device according to claim 1 wherein the projections are rounded, rectangular, trapezoidal or barbed.

12. A device according to claim 1 wherein the bore has a sidewall and the projections do not touch the bore sidewall.

13. A device according to claim 12 wherein the projections have a minimum clearance of about 1 to about 3 mm between the projections and the bore sidewall.

14. A device according to claim 1 wherein the projections reciprocate axially during actuation of the device.

15. A device according to claim 1 wherein moving the nib from its closed position to its open position and then to its closed position also causes the projections to move through at least some of the powder, thereby discouraging clumping, helping to break up already-formed clumps, and encouraging the powder to fall past the nib.

16. A device according to claim 15 wherein the projections move with respect to some but not all of the nearby powder.

17. A device according to claim 1 wherein the projections undergo both movement in the direction of the central axis and a rotational movement around that axis with each device actuation.

18. A device according to claim 1 wherein the actuator and nib are integrally molded.

19. A device according to claim 1 wherein the device permits single instrument gravitationally-assisted powder dispensing without requiring the application of pressure on a cross-section of the powder itself to force powder out of the device, and may be operated from its proximal end to dispense powder while the distal end is inserted in a patient's mouth but does not touch the back of the patient's throat.

20. A device according to claim 1 wherein the device is non-air-assisted, does not aerosolize the dispensed powder, and can be rotated at least 360° around its central axis while in a patient's mouth.

21. A device according to claim 1 wherein the device can be operated with one gloved hand and provides a line of site view enabling a user to see simultaneously the distal end of the device, previously dispensed powder and the area on which powder will be dispensed with the next device actuation.

22. A device according to claim 1 wherein the device keeps its powder dry until such time as dispensed powder contacts a surgical site, and delivers most or all of the dispensed powder to the surgical site and none or substantially none of the dispensed powder to surrounding tissue or a patient airway.

23. A device according to claim 1 wherein the device is in sealed sterilized packaging.

* * * * *